(12) United States Patent
Frenz et al.

(10) Patent No.: US 6,849,665 B2
(45) Date of Patent: Feb. 1, 2005

(54) ABSORBENT COMPOSITIONS

(75) Inventors: Volker Frenz, Mainz-Kostheim (DE); Norbert Herfert, Altenstadt (DE); Ulrich Riegel, Frankfurt (DE); William E. Volz, Suffolk, VA (US); Thomas H. Majette, Portsmouth, VA (US); James Hill, Virginia Beach, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/028,908

(22) Filed: Dec. 28, 2001

(65) Prior Publication Data

US 2002/0165288 A1 Nov. 7, 2002

(30) Foreign Application Priority Data

Dec. 29, 2000  (DE) ......................................... 100 65 252

(51) Int. Cl.$^7$ .................................................. C08J 9/28
(52) U.S. Cl. ....................... 521/64; 424/443; 424/444; 424/448; 428/403; 428/407; 428/304.4; 428/532; 428/533; 428/534
(58) Field of Search ........................... 521/64; 428/403, 428/407, 304.4, 532, 533, 534, 443, 444, 448; 604/358, 369

(56) References Cited

U.S. PATENT DOCUMENTS

| | | | |
|---|---|---|---|
| 5,562,646 A | * | 10/1996 | Goldman et al. |
| 5,669,894 A | * | 9/1997 | Goldman et al. |
| 5,716,707 A | | 2/1998 | Mukaida et al. |
| 6,136,873 A | * | 10/2000 | Hahnle et al. |
| 6,620,889 B1 | | 9/2003 | Mertens et al. |

FOREIGN PATENT DOCUMENTS

| | | |
|---|---|---|
| CA | 2 370 380 | 10/2000 |
| DE | 199 09 653 | 9/2000 |
| WO | 91/11162 | 8/1991 |
| WO | 95/26209 | 10/1995 |
| WO | 99/25393 | 5/1999 |
| WO | 99/38541 | 8/1999 |
| WO | 00/62825 | 10/2000 |
| WO | 00 63295 | 10/2000 |

* cited by examiner

*Primary Examiner*—Morton Foelak
(74) *Attorney, Agent, or Firm*—Oblon, Spivak, McClelland, Maier & Neustadt, P.C.

(57) ABSTRACT

Described is a water-absorbent composition containing from 30 to 100% by weight, based on the water-absorbent composition, of water-insoluble water-swellable hydrogels characterized by the following features:

Centrifuge Retention Capacity (CRC) of at least 24 g/g,

Saline Flow Conductivity (SFC) of at least $80 \times 10^{-7}$ cm$^3$ s/g and

Free Swell Rate (FSR) of at least 0.15 g/g s and/or Vortex Time of not more than 160 s.

15 Claims, No Drawings

ABSORBENT COMPOSITIONS

DESCRIPTION

This invention relates to water-absorbent compositions possessing enhanced permeability, capacity and swell rate, to hygiene articles containing same and to methods for improving the property profile of such hygiene articles.

The use of hydrophilic highly swellable hydrogels in hygiene articles has substantially reduced hygiene article bulk without sacrificing water absorption capacity. The hydrogels were chiefly selected on the basis of their water absorption capacity.

The current trend in diaper design is toward even thinner constructions having a reduced cellulose fiber content and an increased hydrogel content. The advantage of thinner constructions shows itself not only in improved wear comfort, but also in reduced costs for packaging and warehousing. The trend toward ever thinner diaper constructions has substantially changed the profile of properties required of the water-swellable hydrophilic polymers. The decisive property is now the ability of the hydrogel to conduct and distribute imbibed liquid. The greater amount of polymer per unit area in the hygiene article must not cause the swollen polymer to form a barrier layer for subsequent liquid (gel blocking). Good transportation properties on the part of the product is a possible way to ensure optimum utilization of the entire hygiene article.

The gel blocking effect is generally circumvented by providing from the start additional acquisition layers in the hygiene article which imbibe the impinging liquid in the manner of an intermediate buffer and distribute it within the absorption layer, in order to conduct it subsequently into the hydrogels. For instance, WO 91/11162 describes a hygiene article comprising an additional liquid distribution layer composed of chemically crosslinked cellulose fibers.

Through the incorporation of an additional acquisition layer, the liquid is conducted away from the impingement site, is intermediately buffered and then absorbed by the hydrogel material at a rate arrived at through extensive optimization work. The exclusive approach adopted was to focus in particular on Absorbency Under Load (AUL), or more recently Pressure Absorbency Index (PAI) values, and to accept the gel blocking effect, which is observed primarily at high use levels of highly swellable hydrogel particles, as a given and to compensate for it through the incorporation of additional acquisition layers in the hygiene article.

Improved absorption layer permeability is achieved in WO 95/26209 when the highly swellable hydrogels have a Saline Flow Conductivity (SFC) of at least $30 \times 10^{-7}$ cm$^3$ s/g. SFC measures the ability of the hydrogel layer formed to conduct liquid against a given pressure. To achieve the above objective, the highly swellable hydrogels must have a Performance Under Pressure (PUP) of at least 23 g/g. The PUP values are determined as 60 minute absorption values for synthetic urine under a weight of 0.7 psi (5 kPa). Finally, the level of extractables must not be higher than 15%, based on the total polymer content.

However, hygiene articles comprising thin absorbent compositions highly loaded with highly swellable hydrogels continue to have increased leakage rates in practice. There is still a need to provide absorbent compositions which, when used in hygiene articles, have good transportation properties, rapid liquid imbibition coupled with a high ultimate absorption capacity and do not have the disadvantages of the prior art.

It is an object of the present invention to provide absorbent compositions possessing an excellent permeability, a high absorption capacity and a high swell rate, so that the gel blocking effect can be avoided. This fact permits higher loading with highly swellable hydrogels, which in turn makes it possible to manufacture thinner hygiene articles having substantial advantages with regard to wear comfort and logistics.

We have found that this object is achieved according to the invention by a water-absorbent composition containing from 30 to 100% by weight, based on the water-absorbent composition, of water-insoluble water-swellable hydrogels characterized by the following features: Centrifuge Retention Capacity (CRC) of at least 24 g/g, Saline Flow Conductivity (SFC) of at least $80 \times 10^{-7}$ cm$^3$ s/g and Free Swell Rate (FSR) of at least 0.15 g/g s and/or Vortex Time of not more than 160 s.

The present invention further provides a method for improving the performance profile of water-absorbent compositions by enhancing the permeability, capacity and swell rate of the water-absorbent compositions by use of water-insoluble water-swellable hydrogels characterized by the following property spectrum: Centrifuge Retention Capacity (CRC) of at least 24 g/g, Saline Flow Conductivity (SFC) of at least $80 \times 10^{-7}$ cm$^3$ s/g and Free Swell Rate (FSR) of at least 0.15 g/g s and/or Vortex Time of not more than 160 s, in the water-absorbent compositions.

The present invention further provides a method for determining water-absorbent compositions possessing high permeability, capacity and swell rate by measuring the Centrifuge Retention Capacity (CRC), Saline Flow Conductivity (SFC), Free Swell Rate (FSR) and/or Vortex Time for water-insoluble water-swellable hydrogels present in a given water-absorbent composition and determining the water-absorbent compositions whose hydrogels are characterized by the following property spectrum: CRC of at least 24 g/g, SFC of at least $80 \times 10^{-7}$ cm$^3$ s/g and FSR of at least 0.15 g/g s and/or Vortex Time of not more than 160 s.

The invention further provides for the use of water-absorbent compostions containing water-insoluble water-swellable hydrogels characterized by the following features: Centrifuge Retention Capacity (CRC) of at least 24 g/g, Saline Flow Conductivity (SFC) of at least $80 \times 10^{-7}$ cm$^3$ s/g and Free Swell Rate (FSR) of at least 0.15 g/g s and/or Vortex Time of not more than 160 s, in hygiene articles or other articles for absorbing aqueous fluids to enhance the permeability, capacity and swell rate.

It was found that the use of highly swellable hydrogels having a specific features spectrum comprising absorption capacity, absorption rate and permeability makes it possible to produce absorbent compositions having a high hydrogel content whose highly swellable polymer particles are notable for high absorption capacity and good liquid distribution. The use of highly swellable hydrogels having the property combination according to the invention makes it possible to generate an absorbent composition possessing improved permeability and high capacity. Owing to the thus facilitated enhanced content of highly swellable hydrogels of high capacity, the absorbent composition provides an enormous absorption performance, so that even the problem of leakage is circumvented. At the same time, the high absorption capacity is fully utilized.

The term "water-absorbent" relates to water and aqueous systems which may contain organic and inorganic compounds in solution, especially to body fluids such as urine, blood or fluids containing same.

The absorbent composition is useful in hygiene articles, such as diapers, sanitary napkins and incontinence pads for once-only use.

The absorbent composition may preferably have a high content of highly swellable hydrogels, so that the content thereof in the absorbent composition is at least 30% by weight, better at least 50% by weight, preferably at least 60%, more preferably at least 70%, particularly preferably 80% and extremely preferably at least 90%.

The invention employs hydrogels having the following combinations of properties:
CRC≧24 g/g, preferably ≧26 g/g, preferably ≧28 g/g, even more preferably ≧30 g/g, particularly preferably CRC≧32 g/g and most preferably ≧35 g/g and
SFC≧80×10$^{-7}$ cm$^3$ s/g, preferably ≧100×10$^{-7}$ cm$^3$ s/g, more preferably ≧120×10$^{-7}$ cm$^3$ s/g, even more preferably ≧150×10$^{-7}$ cm$^3$ s/g, especially preferably ≧200×10$^{-7}$ cm$^3$ s/g, most preferably ≧300×10$^{-7}$ cm$^3$ s/g, and
Free Swell Rate≧0.15 g/gs, preferably ≧0.20 g/gs, more preferably ≧0.30 g/gs, even more preferably ≧0.50 g/gs, especially preferably ≧0.70 g/gs, most preferably ≧1.00 g/gs or Vortex Time≧160 s, preferably Vortex Time≧120 s, more preferably Vortex Time≧90 s, especially preferably Vortex Time≧60 s, most preferably Vortex Time≧30 s.

The water-swellable hydrogels may be present in conjunction with a base material for the hydrogels. They may preferably be embedded as particles in a polymer fiber matrix or an open-celled polymer foam, but may also be fixed on a sheetlike base material or present as particles in chambers formed from a base material.

In addition, the hydrogels may be coated with a steric or electrostatic spacer.

The water-absorbent compositions for the invention may be produced by
preparing the water-swellable hydrogels,
optionally coating the hydrogels with a steric or electrostatic spacer and
conjoining the hydrogels to the base material, preferably introducing the hydrogels into a polymer fiber matrix or an open-celled polymer foam or into chambers formed from a fiber material or fixing on a sheetlike base material.

The water-absorbent compositions will serve in particular to produce hygiene articles or other examples for absorbing aqueous fluids. Such hygiene articles preferably contain a water-absorbent composition as defined above between a liquid-pervious topsheet and a liquid-impervious backsheet. They can be present in the form of diapers, sanitary napkins and incontinence products such as pads.

The construction of water-swellable hydrogels and their use will now be more particularly described.

Water-Swellable Hydrogels

Hydrogel-forming polymers are in particular polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products that are swellable in aqueous fluids, for example guar derivatives, alginates and carrageenans.

Suitable grafting bases can be of natural or synthetic origin. Examples are starch, cellulose or cellulose derivatives and also other polysaccharides and oligosaccharides, polyvinyl alcohol, polyalkylene oxides, especially polyethylene oxides and polypropylene oxides, polyamines, polyamides and also hydrophilic polyesters. Suitable polyalkylene oxides have for example the formula

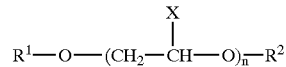

where
R$^1$ and R$^2$ are independently hydrogen, alkyl, alkenyl or aryl,
X is hydrogen or methyl and
n is an integer from 1 to 10 000.
R$^1$ and R$^2$ are each preferably hydrogen, (C$_1$–C$_4$)-alkyl, (C$_2$–C$_6$)-alkenyl or phenyl.

Preferred hydrogel-forming polymers are crosslinked polymers having acid groups which are predominantly in the form of their salts, generally alkali metal or ammonium salts. Such polymers swell particularly strongly on contact with aqueous fluids to form gels.

Preference is given to polymers which are obtained by crosslinking polymerization or copolymerization of acid-functional monoethylenically unsaturated monomers or salts thereof. It is further possible to (co)polymerize these monomers without crosslinkers and to crosslink subsequently.

Examples of such monomers bearing acid groups are monoethylenically unsaturated C$_3$- to C$_{25}$-carboxylic acids or anhydrides such as acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. It is also possible to use monoethylenically unsaturated sulfonic or phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, vinylphosphonic acid, allylphosphonic acid, styrenesulfonic acid and 2-acrylamido-2-methylpropanesulfonic acid. The monomers may be used alone or mixed.

Preferred monomers are acrylic acid, methacrylic acid, vinylsulfonic acid, acrylamidopropanesulfonic acid or mixtures thereof, for example mixtures of acrylic and methacrylic acid, mixtures of acrylic acid and acrylamidopropanesulfonic acid or mixtures of acrylic acid and vinylsulfonic acid.

To optimize properties, it can be sensible to use additional monoethylenically unsaturated compounds which do not bear an acid group but are copolymerizable with the monomers bearing acid groups. Such compounds include for example the amides and nitriles of monoethylenically unsaturated carboxylic acids, for example acrylamide, methacrylamide and N-vinylformamide, N-vinylacetamide, N-methyl-N-vinylacetamide, acrylonitrile and methacrylonitrile. Examples of further suitable compounds are vinyl esters of saturated C$_1$- to C$_4$-carboxylic acids such as vinyl formate, vinyl acetate or vinyl propionate, alkyl vinyl ethers having at least 2 carbon atoms in the alkyl group, for example ethyl vinyl ether or butyl vinyl ether, esters of monoethylenically unsaturated C$_3$- to C$_6$-carboxylic acids, for example esters of monohydric C$_1$- to C$_{18}$-alcohols and acrylic acid, methacrylic acid or maleic acid, monoesters of maleic acid, for example methyl hydrogen maleate, N-vinyllactams such as N-vinyl-pyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses ($M_n$) of the polyalkylene glycols being up to 2 000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

Preference is given to crosslinked polymers of monoethylenically unsaturated monomers which bear acid groups and which are optionally converted into their alkali metal or ammonium salts before or after polymerization and of 0–40% by weight, based on their total weight, of monoethylenically unsaturated monomers which do not bear acid groups.

Preference is given to crosslinked polymers of monoethylenically unsaturated $C_3$–$C_{12}$-carboxylic acids and/or their alkali metal or ammonium salts. Preference is given in particular to crosslinked polyacrylic acids, 25–100% of whose acid groups are present as alkali metal or ammonium salts.

Possible crosslinkers include compounds containing at least two ethylenically unsaturated double bonds. Examples of compounds of this type are N,N'-methylenebisacrylamide, polyethylene glycol diacrylates and polyethylene glycol dimethacrylates each derived from polyethylene glycols having a molecular weight of from 106 to 8 500, preferably from 400 to 2 000, trimethylolpropane triacrylate, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, allyl methacrylate, diacrylates and dimethacrylates of block copolymers of ethylene oxide and propylene oxide, polyhydric alcohols, such as glycerol or pentaerythritol, doubly or more highly esterified with acrylic acid or methacrylic acid, triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols having a molecular weight of from 106 to 4 000, trimethylolpropane diallyl ether, butanediol divinyl ether, pentaerythritol triallyl ether, reaction products of 1 mol of ethylene glycol diglycidyl ether or polyethylene glycol diglycidyl ether with 2 mol of pentaerythritol triallyl ether or allyl alcohol, and/or divinylethyleneurea. Preference is given to using water-soluble crosslinkers, for example N,N'-methylenebisacrylamide, polyethylene glycol diacrylates and polyethylene glycol dimethacrylates derived from addition products of from 2 to 400 mol of ethylene oxide with 1 mol of a diol or polyol, vinyl ethers of addition products of from 2 to 400 mol of ethylene oxide with 1 mol of a diol or polyol, ethylene glycol diacrylate, ethylene glycol dimethacrylate or triacrylates and trimethacrylates of addition products of from 6 to 20 mol of ethylene oxide with 1 mol of glycerol, pentaerythritol triallyl ether and/or divinylurea.

Possible crosslinkers also include compounds containing at least one polymerizable ethylenically unsaturated group and at least one further functional group. The functional group of these crosslinkers has to be capable of reacting with the functional groups, essentially the acid groups, of the monomers. Suitable functional groups include for example hydroxyl, amino, epoxy and aziridino groups. Useful are for example hydroxyalkyl esters of the abovementioned monoethylenically unsaturated carboxylic acids, e.g., 2-hydroxyethyl acrylate, hydroxypropyl acrylate, hydroxybutyl acrylate, hydroxyethyl methacrylate, hydroxypropyl methacrylate and hydroxybutyl methacrylate, allylpiperidinium bromide, N-vinylimidazoles, for example N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. It is also possible to use dialkylaminoalkyl acrylates and dialkylaminoalkyl methacrylates such as dimethylaminoethyl acrylate, dimethylaminoethyl methacrylate, diethylaminoethyl acrylate and diethylaminoethyl methacrylate. The basic esters are preferably used in quaternized form or as salt. It is also possible to use glycidyl (meth)acrylate, for example.

Useful crosslinkers further include compounds containing at least two functional groups capable of reacting with the functional groups, essentially the acid groups, of the monomers. Suitable functional groups were already mentioned above, i.e., hydroxyl, amino, epoxy, isocyanate, ester, amido and aziridino groups. Examples of such crosslinkers are ethylene glycol, diethylene glycol, triethylene glycol, tetraethylene glycol, polyethylene glycol, glycerol, polyglycerol, triethanolamine, propylene glycol, polypropylene glycol, block copolymers of ethylene oxide and propylene oxide, ethanolamine, sorbitan fatty acid esters, ethoxylated sorbitan fatty acid esters, trimethylolpropane, pentaerythritol, 1,3-butanediol, 1,4-butanediol, polyvinyl alcohol, sorbitol, starch, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, diphenylmethanebis-4,4'-N,N'-diethyleneurea, halo epoxy compounds such as epichlorohydrin and α-methylepifluorohydrin, polyisocyanates such as 2,4-toluylene diisocyanate and hexamethylene diisocyanate, alkylene carbonates such as 1,3-dioxolan-2-one and 4-methyl-1,3-dioxolan-2-one, also bisoxazolines and oxazolidones, polyamidoamines and also their reaction products with epichlorohydrin, also polyquaternary amines such as condensation products of dimethylamine with epichlorohydrin, homo- and copolymers of diallyldimethylammonium chloride and also homo- and copolymers of dimethylaminoethyl (meth)acrylate which are optionally quaternized with, for example, methyl chloride.

Useful crosslinkers further include polyvalent metal ions capable of forming ionic crosslinks. Examples of such crosslinkers are magnesium, calcium, barium and aluminum ions. These crosslinkers are used for example as hydroxides, carbonates or bicarbonates. Useful crosslinkers further include multifunctional bases likewise capable of forming ionic crosslinks, for example polyamines or their quaternized salts. Examples of polyamines are ethylenediamine, diethylenetriamine, triethylenetetramine, tetraethylenepentamine, pentaethylenehexamine and polyethyleneimines and also polyamines having molar masses in each case of up to 4 000 000.

The crosslinkers are present in the reaction mixture for example from 0.001 to 20%, preferably from 0.01 to 14%, by weight.

The polymerization is initiated in the generally customary manner, by means of an initiator. But the polymerization may also be initiated by electron beams acting on the polymerizable aqueous mixture. However, the polymerization may also be initiated in the absence of initiators of the abovementioned kind, by the action of high energy radiation in the presence of photoinitiators. Useful polymerization initiators include all compounds which decompose into free radicals under the polymerization conditions, for example peroxides, hydroperoxides, hydrogen peroxides, persulfates, azo compounds and redox catalysts. The use of water-soluble initiators is preferred. In some cases it is advantageous to use mixtures of different polymerization initiators, for example mixtures of hydrogen peroxide and sodium peroxodisulfate or potassium peroxodisulfate. Mixtures of hydrogen peroxide and sodium peroxodisulfate may be used in any proportion. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide and tert-amyl perneodecanoate. Particularly suitable polymerization initiators are water-soluble azo initiators, e.g., 2,2'-azobis(2-amidinopropane) dihydrochloride, 2,2'-azobis(N,N'-dimethylene)isobutyramidine dihydrochloride, 2-(carbamoylazo)isobutyronitrile, 2,2'-azobis[2-(2'-imidazolin-2-yl)propane] dihydrochloride and 4,4'-azobis(4-cyanovaleric acid). The polymerization initiators mentioned are used in customary amounts, for example in amounts of from 0.01 to 5%, preferably from 0.05 to 2.0%, by weight, based on the monomers to be polymerized.

Useful initiators also include redox catalysts. In redox catalysts, the oxidizing component is at least one of the above-specified per compounds and the reducing component is for example ascorbic acid, glucose, sorbose, ammonium or alkali metal bisulfite, sulfite, thiosulfate, hyposulfite, pyrosulfite or sulfide, or a metal salt, such as iron(II) ions or sodium hydroxymethylsulfoxylate. The reducing component in the redox catalyst is preferably ascorbic acid or sodium sulfite. Based on the amount of monomers used in the polymerization, from $3 \times 10^{-6}$ to 1 mol % may be used for the reducing component of the redox catalyst system and from 0.001 to 5.0 mol % for the oxidizing component of the redox catalyst, for example.

When the polymerization is initiated using high energy radiation, the initiator used is customarily a photoinitiator. Photoinitiators include for example α-splitters, H-abstracting systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the abovementioned free-radical formers, substituted hexaarylbisimidazoles or acylphosphine oxides. Examples of azides are:

2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. Photoinitiators, if used, are customarily used in amounts of from 0.01 to 5% of the weight of the monomers to be polymerized.

The subsequent crosslinking stage comprises polymers which were prepared by polymerization of the abovementioned monoethylenically unsaturated acids and optionally monoethylenically unsaturated comonomers and which have a molecular weight of more than 5 000, preferably more than 50 000, being reacted with compounds having at least two groups which are reactive toward acid groups. This reaction can take place at room temperature or else at elevated temperatures of up to 220° C.

Suitable functional groups were already mentioned above, i.e., hydroxyl, amino, epoxy, isocyanate, ester, amido and aziridino groups, as well examples of such crosslinkers.

Useful postcrosslinkers further include polyvalent metal ions capable of forming ionic crosslinks. Examples of such crosslinkers are recited above. Useful crosslinkers further include multifunctional bases likewise capable of forming ionic crosslinks; hereto examples of such compounds are mentioned above.

Crosslinkers are added to the acid-functional polymers or salts in amounts of from 0.5 to 25% by weight, preferably from 1 to 15% by weight, based on the amount of polymer used.

Crosslinked polymers are preferably used in fully neutralized form. However, neutralization may also be partial only. The degree of neutralization is preferably within the range from 25 to 100%, especially within the range from 50 to 100%. Useful neutralizing agents include alkali metal bases or ammonia/amines. Preference is given to the use of aqueous sodium hydroxide solution or aqueous potassium hydroxide solution. However, neutralization may also be effected using sodium carbonate, sodium bicarbonate, potassium carbonate or potassium bicarbonate or other carbonates or bicarbonates or ammonia. Moreover primary, secondary and tertiary amines may be used.

Industrial processes useful for making these products include all processes which are customarily used to make superabsorbents, as described for example in Chapter 3 of "Modern Superabsorbent Polymer Technology", F. L. Buchholz and A. T. Graham, Wiley-VCH, 1998.

Polymerization in aqueous solution is preferably conducted as a gel polymerization. It involves 10–70% strength by weight aqueous solutions of the monomers and optionally of a suitable grafting base being polymerized in the presence of a free-radical initiator by utilizing the Trommsdorff-Norrish effect.

The polymerization reaction may be carried out at from 0 to 150° C., preferably at from 10 to 100° C., not only at atmospheric pressure but also at superatmospheric or reduced pressure. As is customary, the polymerization may also be conducted in a protective gas atmosphere, preferably under nitrogen.

By subsequently heating the polymer gels at from 50 to 130° C., preferably at from 70 to 100° C., for several hours, the performance characteristics of the polymers can be further improved.

Preference is given to hydrogel-forming polymers which have been surface postcrosslinked. Surface postcrosslinking may be carried out in a conventional manner using dried, ground and classified polymer particles.

To effect surface postcrosslinking, compounds capable of reacting with the functional groups of the polymers by crosslinking are applied to the surface of the hydrogel particles, preferably in the form of an aqueous solution. The aqueous solution may contain water-miscible organic solvents. Suitable solvents are alcohols such as methanol, ethanol, i-propanol or acetone.

Suitable surface postcrosslinkers include for example:

di- or polyglycidyl compounds such as diglycidyl phosphonates or ethylene glycol diglycidyl ether, bischlorohydrin ethers of polyalkylene glycols, alkoxysilyl compounds, polyaziridines, aziridine compounds based on polyethers or substituted hydrocarbons, for example bis-N-aziridinomethane, polyamines or polyamidoamines and their reaction products with epichlorohydrin, polyols such as ethylene glycol, 1,2-propanediol, 1,4-butanediol, glycerol, methyltriglycol, polyethylene glycols having an average molecular weight $M_w$ of 200–10 000, di- and polyglycerol, pentaerythritol, sorbitol, the ethoxylates of these polyols and their esters with carboxylic acids or carbonic acid such as ethylene carbonate or propylene carbonate, carbonic acid derivatives such as urea, thiourea, guanidine, dicyandiamide, 2-oxazolidinone and its derivatives, bisoxazoline, polyoxazolines, di- and polyisocyanates, di- and poly-N-methylol compounds such as, for example, methylenebis(N-methylolmethacrylamide) or melamine-formaldehyde resins, compounds having two or more blocked isocyanate groups such as, for example, trimethylhexamethylene diisocyanate blocked with 2,2,3,6-tetramethylpiperidin-4-one.

If necessary, acidic catalysts may be added, for example p-toluenesulfonic acid, phosphoric acid, boric acid or ammonium dihydrogenphosphate.

Particularly suitable surface postcrosslinkers are di- or polyglycidyl compounds such as ethylene glycol diglycidyl ether, the reaction products of polyamidoamines with epichlorohydrin and 2-oxazolidinone.

The crosslinker solution is preferably applied by spraying with a solution of the crosslinker in conventional reaction mixers or mixing and drying equipment such as Patterson-Kelly mixers, DRAIS turbulence mixers, Lödige mixers, screw mixers, plate mixers, fluidized bed mixers and Schugi Mix. The spraying of the crosslinker solution may be followed by a heat treatment step, preferably in a downstream dryer, at from 80 to 230° C., preferably 80–190° C., particularly preferably at from 100 to 160° C., for from 5 minutes to 6 hours, preferably from 10 minutes to 2 hours, particularly preferably from 10 minutes to 1 hour, during which not only cracking products but also solvent fractions can be removed. But the drying may also take place in the mixer itself, by heating the jacket or by blowing in a preheated carrier gas.

In a particularly preferred embodiment of the invention, the hydrogel-forming polymer is subsequently coated with a steric or electrostatic spacer. Useful steric spacers include inert materials (powders), for example silicates having a band, chain or sheet structure (montmorillonite, kaolinite, talc), zeolites, active carbons or silicas. Inorganic inert spacers further include for example magnesium carbonate, calcium carbonate, barium sulfate, aluminum oxide, titanium dioxide and iron(II) oxide. Organic inert spacers include for example polyalkyl methacrylates or thermoplastics such as for example polyvinyl chloride. Preference is given to using silicas, which divide into precipitated silicas and pyrogenic silicas according to their method of preparation. Both variants are commercially available under the name AEROSIL® (pyrogenic silicas) or Silica FK, Sipernat®, Wessalon® (precipitated silica). Precipitated silicas are used with particular preference. The hydrogel-forming polymers coated with inert spacer material may be produced by applying the inert spacers in an aqueous or water-miscible medium or else by applying the inert spacers in powder form to pulverulent hydrogel-forming polymer material. The aqueous or water-miscible media are preferably applied by spraying onto dry polymer powder. In a particularly preferred version of the production process, pure powder/powder blends are produced from pulverulent inert spacer material and hydrogel-forming polymer. The inert spacer material is applied to the surface of the hydrogel-forming polymer in a proportion of 0.05 to 5% by weight, preferably from 0.1 to 1.5% by weight, particularly preferably from 0.3 to 1% by weight, based on the total weight of the coated hydrogel.

Cationic components may be added as electrostatic spacers. It is generally possible to add cationic polymers for the purpose of electrostatic repulsion. This is accomplished for example with polyalkylenepolyamines, cationic derivatives of polyacrylamides, polyethyleneimines, polyquaternary amines, for example condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and β-methacrylyloxyethyltrimethylammonium chloride, hydroxycellulose reacted with epichlorohydrin and then quaternized with trimethylamine, homopolymers of diallyldimethylammonium chloride or addition products of epichlorohydrin with amidoamines. Polyquaternary amines may further be synthesized by reaction of dimethyl sulfate with polymers, such as polyethyleneimines, copolymers of vinylpyrrolidone and dimethylaminoethyl methacrylate or copolymers of ethyl methacrylate and diethylaminoethyl methacrylate. Polyquaternary amines are available in a wide molecular weight range.

Electrostatic spacers are also generated by applying a crosslinked, cationic sheath, either by means of reagents capable of forming a network with themselves, for example addition products of epichlorohydrin with polyamidoamines, or by applying cationic polymers capable of reacting with an added crosslinker, for example polyamines or polyimines combined with polyepoxides, multifunctional esters, multifunctional acids or multifunctional (meth)acrylates. It is also possible to use any multifunctional amines having primary or secondary amino groups, for example polyethyleneimine, polyallylamine, polylysine, preferably polyvinylamine. Further examples of polyamines are ethylenediamine, diethylenetriamine, triethylenetetramine, tetraethylenepentamine, pentaethylenehexamine and polyethyleneimines and also polyamines having molar masses of up to 4 000 000 in each case.

Electrostatic spacers may also be applied by adding solutions of divalent or more highly valent metal salt solutions. Examples of divalent or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$, preferred metal cations are $Mg^{2+}$, $Ca^{2+}$, $Al^{3+}$, $Ti^{4+}$, $Zr^{4+}$ and $La^{3+}$ and particularly preferred metal cations are $Al^{3+}$, $Ti^{4+}$ and $Zr^{4+}$. The metal cations may be used not only alone but also mixed with each other. Of the metal cations mentioned, all salts are suitable that possess adequate solubility in the solvent to be used. Of particular suitability are metal salts with weakly complexing anions such as for example chloride, nitrate and sulfate. Useful solvents for the metal salts include water, alcohols, DMF, DMSO and also mixtures thereof. Particular preference is given to water and water-alcohol mixtures, for example water-methanol or water-1,2-propanediol.

In the production process, the electrostatic spacers may be applied like the inert spacers by application in an aqueous or water-miscible medium. This is the preferred production process in the case of the addition of metal salts. Cationic polymers are applied to pulverulent hydrogel-forming polymer material by applying an aqueous solution or in a water-miscible solvent, optionally also as dispersion, or else by application in powder form. The aqueous or water-miscible media are preferably applied by spraying onto dry polymer powder. The polymer powder may optionally be subsequently dried. The cationic spacers are applied to the surface of the hydrogel-forming polymer in a proportion of from 0.05 to 5% by weight, preferably from 0.1 to 1.5% by weight, particularly preferably from 0.1 to 1% by weight, based on the total weight of the coated hydrogel.

The highly swellable (water-swellable) hydrogels may be combined with structurants to form the water-absorbent composition. Useful structurants include for example a fiber matrix comprising a cellulose fiber mix (airlaid web, wet laid web) or synthetic polymer fibers (meltblown web, spunbonded web) or else a blend of cellulose fibers and synthetic fibers. It is further possible to use open-celled foams or the like for incorporating highly swellable hydrogels.

Alternatively, such a construction can be the result of fusion of two individual layers, forming one or better a multiplicity of chambers to contain the highly swellable hydrogels. In this case, at least one of the two layers should be water-pervious. The second layer can be either water-pervious or water-impervious. The layer material can be tissues or other fabric, closed-celled or open-celled foams, perforated films, elastomers or fabrics composed of fiber material. If the absorbent composition is a construction formed by layers, the layer material should have a pore structure whose pore dimensions are small enough to retain the highly swellable hydrogel particles. The above examples relating to the construction of the absorbent composition also include laminates of at least two layers between which the highly swellable hydrogels are installed and fixed.

Furthermore, the absorbent composition may comprise a base material, for example a polymer film, on which the highly swellable hydrogel particles are fixed. The fixing may be effected not only on one side but also on both sides. The base material can be water pervious or water impervious.

The above absorbent compositions incorporate the highly swellable hydrogels at a weight fraction of from 30 to 100% by weight, better from 50 to 100% by weight, preferably from 60 to 100% by weight, more preferably from 70 to 100% by weight, particularly preferably from 80 to 100% by weight, extremely preferably from 90 to 100% by weight, based on the total weight of the composition.

If the above absorbent composition construction is a fiber matrix, then the absorbent composition results from a mixture of fiber materials and highly swellable hydrogels. This fiber mixture incorporates the highly swellable hydrogels at a weight fraction of preferably not less than 30% by weight, better not less than 50% by weight, more preferably not less than 60% by weight, based on the total weight of the absorbent composition.

The structure of the present absorbent composition according to the invention may be based on various fiber materials, which are used as a fiber network or matrices. The present invention includes not only fibers of natural origin (modified or unmodified) but also synthetic fibers.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyesters fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9 000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the invention can be hydrophilic and/or hydrophobic. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent composition of the invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557 H, Hercoles, Inc. Wilmington, Del.), polyacrylamide coatings (described in U.S. Pat. No. 3,556,932 or as the Parez® 631 NC commercial product from American Cyanamid Co., Stamford, Conn.), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimension stability is imparted as a result of this treatment. In addition to their hydrophlic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. No. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Examples of processes to obtain an absorbent composition comprising for example a fiber material blend of synthetic fibers (a) and cellulose fibers (b) embedded in highly swellable hydrogels (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted.

Description of Test Methods

Centrifuge Retention Capacity (CRC)

This method measures the free swellability of the hydrogel in a teabag. 0.2000±0.0050 g of dried hydrogel (particle size fraction 106–850 μm) is sealed into a teabag 60×85 mm in size. The teabag is then soaked for 30 minutes in an excess of 0.9% by weight sodium chloride solution (at least 0.83 l of sodium chloride solution/1 g of polymer powder). The teabag is then centrifuged for three minutes at 250 g. The amount of liquid is determined by weighing the centrifuged teabag.

Free Swell Rate (FSR)

1.00 g ($W_H$) of hydrogel is uniformly spread out on the bottom of a plastic weighing boat having a round bottom of about 6 cm. The plastic weighing boat is round and about 6 cm in diameter at the bottom, about 2.5 cm deep and about 7.5 cm×7.5 cm square at the top. A funnel is then used to add 20 g ($W_U$) of a synthetic urine solution preparable by dissolving 2.0 g of KCl, 2.0 g of $Na_2SO_4$, 0.85 g of $NH_4H_2PO_4$, 0.15 g of $(NH_4)_2HPO_4$, 0.19 g of $CaCl_2$, and 0.23 g of $MgCl_2$ in 1 liter of distilled water to the center of the weighing boat. The time for the hydrogel to absorb all of the fluid, as indicated by the absence of pooled fluid, is recorded and noted as $t_A$. The Free Swell Rate then computes from $$FSR=W_U/(W_H \times t_A)$$

Saline Flow Conductivity (SFC)

The test method for determining SFC is described in WO 95/26209.

Vortex Time 50 ml of 0.9% by weight NaCl solution are measured into a 100 ml beaker. While the saline solution is being stirred with a magnetic stirrer at 600 rpm, 2.00 g of hydrogel is poured in quickly in such a way that clumping is avoided. The time in seconds is taken for the vortex created by the stirring to close and for the surface of the saline solution to become flat.

Acquisition Time/Rewet Under Pressure

The test is carried out using laboratory pads. To produce these laboratory pads, 11.2 g of cellulose fluff and 23.7 g of hydrogel are homogeneously fluidized in an air box and by application of a slight vacuum laid down on a mold 12 by 26 cm in size. This composition is then wrapped in tissue paper and compressed for 2 times 15 seconds under a pressure of 200 bar. A laboratory pad produced in this way is attached to a horizontal surface. The center of the pad is determined and marked. Synthetic urine solution is applied through a plate of plastic having a ring in the middle (internal diameter of ring: 6.0 cm, height: 4.0 cm). The plate is loaded with additional weights so that the total load on the pad is 13.6 g/cm². The plate of plastic is placed on the pad in such a way that the center of the pad is also the center of the application ring. 100 ml of 0.9% by weight sodium chloride solution are applied 3 times. The sodium chloride solution is measured out in a measuring cylinder and applied in one shot to the pad through the ring in the plate. At the same time, the time is measured until the solution has completely penetrated into the pad. The time measured is recorded as Acquisition Time 1. Thereafter the pad is weighted with a plate for 20 min, the load being further maintained at 13.6 g/cm². Thereafter the plate is removed, 10 g±0.5 g of filter paper (Schleicher & Schuell, 1450 CV) are placed on the central spot and loaded with a weight (area 10×10 cm, weight 3.5 kg) for 15 s. After this period the weight is removed, and the filter paper is reweighed. The weight difference is noted as Rewet 1. Thereafter the plastic plate with application ring is again placed on the pad and the liquid is applied for the second time. The time measured is noted as Acquisition Time 2. The procedure is repeated as described, but 45 g±0.5 g of filter paper are used for the Rewet test. Rewet 2 is noted. The same method is employed to determine Acquisition Time 3. 50 g±0.5 g of filter paper are used to determine Rewet 3.

The examples which follow illustrate the invention.

EXAMPLES

Testing was carried out on highly swellable hydrogels marked A to K in the tables below.

Samples C, F, I and J are comparative samples which do not conform to the selection criteria of the invention and thus cannot satisfy the absorbent compositions of the invention.

It is very clear to see that these products give test performances with regard to Acquisition Time and Rewet especially on the third application of the synthetic urine solution (Acquisition Time 3, Rewet 3) that differ enormously from those of products conforming to the selection criteria of the invention.

Examples:
Hydrogels tested:

| Product | CRC | SFC | Free Swell Rate | Vortex Time |
|---|---|---|---|---|
| A | 27.2 g/g | 160 × 10⁻⁷ cm³ s/g | 0.25 g/gs | |
| B | 25.8 g/g | 210 × 10⁻⁷ cm³ s/g | | 105 s |
| C | 24.9 g/g | 280 × 10⁻⁷ cm³ s/g | 0.10 g/gs | |
| D | 28.9 g/g | 115 × 10⁻⁷ cm³ s/g | | 80 s |
| E | 29.5 g/g | 100 × 10⁻⁷ cm³ s/g | 0.56 g/gs | |
| F | 29.2 g/g | 35 × 10⁻⁷ cm³ s/g | 0.52 g/gs | |
| G | 32.6 g/g | 95 × 10⁻⁷ cm³ s/g | | 58 s |
| H | 35.4 g/g | 90 × 10⁻⁷ cm³ s/g | | 45 s |
| I | 34.0 g/g | 20 × 10⁻⁷ cm³ s/g | | 35 s |
| J | 22.3 g/g | 250 × 10⁻⁷ cm³ s/g | 0.22 g/gs | |
| K | 25.6 g/g | 330 × 10⁻⁷ cm³ s/g | | 20 s |

Results of Acquisition Time/Rewet test:

| Product | Acquisition Time 1 | Acquisition Time 2 | Acquisition Time 3 | Rewet 1 | Rewet 2 | Rewet 3 |
|---|---|---|---|---|---|---|
| A | 23 s | 53 s | 94 s | <0.1 g | 0.5 g | 2.6 g |
| B | 25 s | 48 s | 72 s | <0.1 g | 0.6 g | 2.9 g |
| C | 22 s | 52 s | 125 s | <0.1 g | 0.9 g | 4.2 g |
| D | 26 s | 55 s | 78 s | <0.1 g | 0.4 g | 1.8 g |
| E | 28 s | 54 s | 83 s | <0.1 g | 0.5 g | 2.1 g |
| F | 27 s | 56 s | 144 s | <0.1 g | 0.5 g | 3.7 g |
| G | 29 s | 55 s | 90 s | <0.1 g | 0.3 g | 1.6 g |
| H | 26 s | 58 s | 94 s | <0.1 g | 0.4 g | 1.3 g |
| I | 29 s | 63 s | 159 s | <0.1 g | 0.5 g | 3.9 g |
| J | 24 s | 44 s | 88 s | <0.1 g | 0.9 g | 5.2 g |
| K | 24 s | 38 s | 64 s | <0.1 g | 0.6 g | 2.8 g |

We claim:

1. A water-absorbent composition comprising from 30 to 100% by weight, based on the water-absorbent composition, of water-insoluble water-swellable hydrogels characterized by the following features:

Centrifuge Retention Capacity (CRC) of at least 24 g/g,

Saline Flow Conductivity (SFC) of at least 80×10⁻⁷ cm³ s/g and

Free Swell Rate (FSR) of at least 0.15 g/g s and/or Vortex Time of not more than 160 s.

2. A water-absorbent composition as claimed in claim 1, wherein the water-swellable hydrogels are present in conjunction with a base material for the hydrogels.

3. A water-absorbent composition as claimed in claim 2, wherein the water-swellable hydrogels are embedded as particles in a polymer fiber matrix or an open-celled polymer foam, fixed on a sheetlike base material or present as particles in chambers formed from a base material.

4. A water-absorbent composition as claimed in claim 1, wherein the hydrogels are coated with a steric or electrostatic spacer.

5. A process for producing water-absorbent compositions as claimed in claim 2 comprising preparing the water-swellable hydrogels, conjoining the hydrogels to a base material.

6. A method of producing hygiene articles or other articles for absorbing aqueous fluids, comprising joining the water-absorbent compositions as claimed in claim 1 with at least one other material.

7. Hygiene articles comprising a water-absorbent composition as claimed in claim 1 between a liquid-pervious topsheet and a liquid-impervious backsheet.

8. Hygiene articles as claimed in claim 7 which are diapers, sanitary napkins, or incontinence products.

9. A method for improving the performance profile of water-absorbent compositions by enhancing the permeability, capacity and swell rate of the water-absorbent compositions comprising incorporating a water-insoluble water-swellable hydrogels characterized by the following property spectrum:

Centrifuge Retention Capacity (CRC) of at least 24 g/g,

Saline Flow Conductivity (SFC) of at least $80 \times 10^{-7}$ cm$^3$ s/g and

Free Swell Rate (FSR) of at least 0.15 g/g s and/or Vortex Time of not more than 160 s into the water-absorbent composition.

10. A method for determining water-absorbent compositions possessing high permeability, capacity and swell rate comprising measuring the Centrifuge Retention Capacity (CRC), Saline Flow Conductivity (SFC), Free Swell Rate (FSR) and/or Vortex Time for water-insoluble water-swellable hydrogels present in a given water-absorbent composition; and determining the water-absorbent compositions wherein the hydrogels are characterized by the following property spectrum:

CRC of at least 24 g/g,

SFC of at least $80 \times 10^{-7}$ cm$^3$ s/g and

FSR of at least 0.15 g/g s and/or Vortex Time of not more than 160 s.

11. A method of producing hygiene articles or other articles for absorbing aqueous fluids, comprising joining at least one other material with the water-absorbent compositions of claim 3:

to enhance the permeability, capacity and swell rate of said articles.

12. A water-absorbent composition as claimed in claim 2, wherein the hydrogels are coated with a steric or electrostatic spacer.

13. A water-absorbent composition as claimed in claim 3, wherein the hydrogels are coated with a steric or electrostatic spacer.

14. The process for producing water-absorbent compositions according to claim 5, further comprising coating the hydrogels with a steric or electrostatic spacer.

15. The process for producing water-absorbent compositions according to claim 5, said hydrogels are conjoined to said base material by introducing the hydrogels into a polymer fiber matrix or an open-celled polymer foam or into chambers formed from a base material or fixing on a sheet-like base material.

* * * * *